United States Patent [19]
Tovey et al.

[11] Patent Number: 5,368,589
[45] Date of Patent: Nov. 29, 1994

[54] SCALPEL GAUGE

[75] Inventors: H. Jonathan Tovey, Milford; Robert W. Churinetz, West Haven; Timothy M. Lohnes, Milford, all of Conn.

[73] Assignee: United States Surgical Corporation, Norwalk, Conn.

[21] Appl. No.: 957,731

[22] Filed: Oct. 7, 1992

[51] Int. Cl.⁵ ............................. A61B 17/00
[52] U.S. Cl. ........................ 606/1; 606/167; D24/146; D10/64
[58] Field of Search ............ 606/167, 172, 166, 148, 606/150, 1; 128/898; 33/566, 565, 562, 563; D24/146; D10/64

[56] References Cited

U.S. PATENT DOCUMENTS

| D. 22,531 | 6/1893 | Ford | D10/64 |
|---|---|---|---|
| D. 32,156 | 1/1900 | Johnson | D10/64 |
| 1,034,547 | 8/1912 | Welsh | D10/64 |
| 3,376,650 | 4/1968 | Cook | 33/566 |
| 4,406,285 | 9/1983 | Villasenor et al. | 606/166 |
| 4,502,815 | 6/1985 | Marinoff | 606/166 |

OTHER PUBLICATIONS

Rapidesign, Inc., No. 22 ABC Template Brochure, Jun. 1, 1949.

*Primary Examiner*—Tamara L. Graysay

[57] ABSTRACT

A surgical template for forming an incision of a predetermined size in tissue, includes a plate member and a plurality of slotted openings or recesses formed in a peripheral edge of the plate member. The slotted openings or recesses may be configured and adapted for reception of at least a portion of a cutting edge of an incising instrument and for guiding the instrument during incising of the tissue. The template may also be used to measure the size of an incision formed by the surgeon.

15 Claims, 4 Drawing Sheets

SCALPEL GAUGE

BACKGROUND OF THE INVENTION

1. Field of the Invention

This invention relates generally to surgical devices, and, in particular to a surgical template to assist in forming incisions of a predetermined size in tissue.

2. Description of the Prior Art

An incision is a cut made in tissue with a scalpel or a similar incising instrument to access the surgical objective. Typically, the cutting edge of the scalpel is applied to the operative site, and, with the application of a downward force and sliding motion the tissue is incised. In most operative procedures, the incision is made "freehand" with no assistance from mechanical aids or guiding devices.

In abdominal surgery, the abdominal cavity is incised to gain access to an organ or bodily part within the cavity. In accordance with such procedures, one or more incisions are made in the abdominal cavity and the peritoneum which lines the cavity. The incised tissue is thereafter split and separated to provide an approach to the surgical site.

Recently, there has been emphasis placed on performing abdominal surgery utilizing laparoscopic techniques. In accordance with such techniques, a cannula or trocar sleeve is inserted within an incision in the body cavity, and the surgery is performed with instruments that are inserted through the cannula. The incision is typically formed with a sharp pointed trocar which is inserted within the cannula and then removed. The trocar is configured to form a symmetrical incision of a predetermined dimension.

Forming consistently dimensioned incisions is a significant objective in laparoscopic surgery. In surgery of this type the incision is desirably sized to approximate the operative dimensions of the instruments to be used therein. In some instances, the incision is dimensioned to form a snug fit between the tissue and the cannula. A snug fit will minimize release of fluids from the body. Furthermore, since laparoscopic surgery requires insufflating gases to raise the cavity wall away from the organs, a snug fit around the cannula will assist in minimizing escape of these gases.

Although conventional trocars will form an incision of a desired dimension in the abdominal cavity, the surgeon may want to use a scalpel to provide improved control over the depth of the incision.

However, with methods known heretofore, the use of a scalpel to form an incision for subsequent insertion of a cannula or other surgical instrument presents some shortcomings. In particular, it is difficult to consistently form an incision with the scalpel to a precise dimension.

The present invention is directed to a device which can be used with a scalpel to form consistent incisions in tissue with great accuracy.

SUMMARY OF THE INVENTION

The present invention provides a surgical template for forming an incision of a predetermined size in body tissue. The template comprises a plate member and guide means associated with the plate member for receiving at least a portion of a cutting edge of an incising instrument and for guiding the instrument during incising of the tissue. The guide means may be in the form of slotted openings or recesses, the recesses being formed along a peripheral edge of the plate member. The slotted openings or recesses vary in dimension to accommodate formation of various sized incisions.

In a preferred embodiment, the template comprises a plate member having a bend line, preferably, generally disposed at the center of the plate member. The bend line defines a first and a second plate portion. A plurality of slotted openings or recesses are provided in at least one plate portion. Each of the slotted openings or recesses is configured and adapted for reception of at least a portion of the cutting edge of an incising instrument and for guiding the instrument during incising of the tissue. In the preferred embodiment, the first and second plate portions define planes which intersect. Accordingly, in use and upon application of one plate portion against the tissue to be incised, the other plate portion projects from the surface of the tissue and, as such, may be grasped by the user to steady the template or to maneuver it into position on the tissue.

The present invention may also be used to measure the size of an incision formed by the surgeon. In accordance with this embodiment, adjacent recesses formed along a peripheral edge of the plate member are dimensioned to define co-planar extensions therebetween. The extensions are adapted for measuring the length of the incision. Preferably, the extensions vary in increments to accommodate measurement of various-sized incisions.

The present invention also provides a method for forming an incision in tissue. The method comprises the steps of providing a surgical template including a plate member having a first and a second portion. At least one of the portions includes guide means. The method further comprises the steps of applying the surgical template to the tissue such that one plate portion is pressed against the tissue and the other plate portion projects from the surface of the tissue, grasping the projecting plate portion along an outer peripheral area thereof and positioning the template on the surface of the tissue to align the desired-sized guide means over the targeted portion of the tissue, inserting a cutting edge of an incising instrument within the slotted opening and incising the tissue by applying a downward force to the instrument and sliding the instrument through the guide means while firmly holding the projecting plate portion in a manner so that the template is pressed against the tissue surface.

BRIEF DESCRIPTION OF THE DRAWINGS

The accompanying drawings, referred to herein and constituting a part hereof, illustrate preferred embodiments of the present invention, and together with the description, serve to explain the principles of the present invention.

DETAILED DESCRIPTION OF THE PREFERRED EMBODIMENTS

Figure 2:
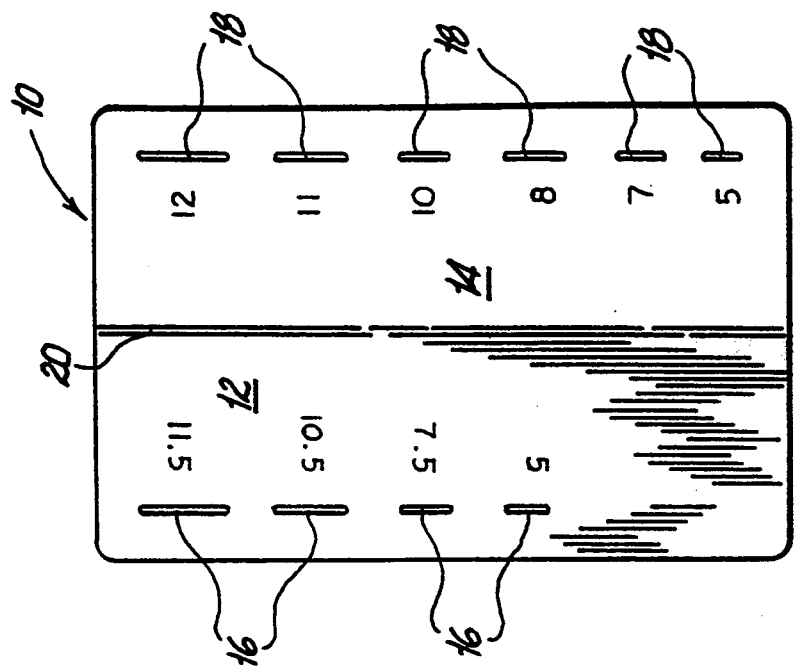
FIG. 2 is a top plan view of the embodiment of FIG. 1.
Figure 3:
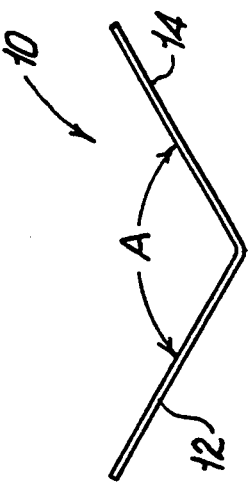
FIG. 3 is an end elevational view of the embodiment of FIG. 1, illustrating the angular relationship between the first and second plate portions.
Figure 1:
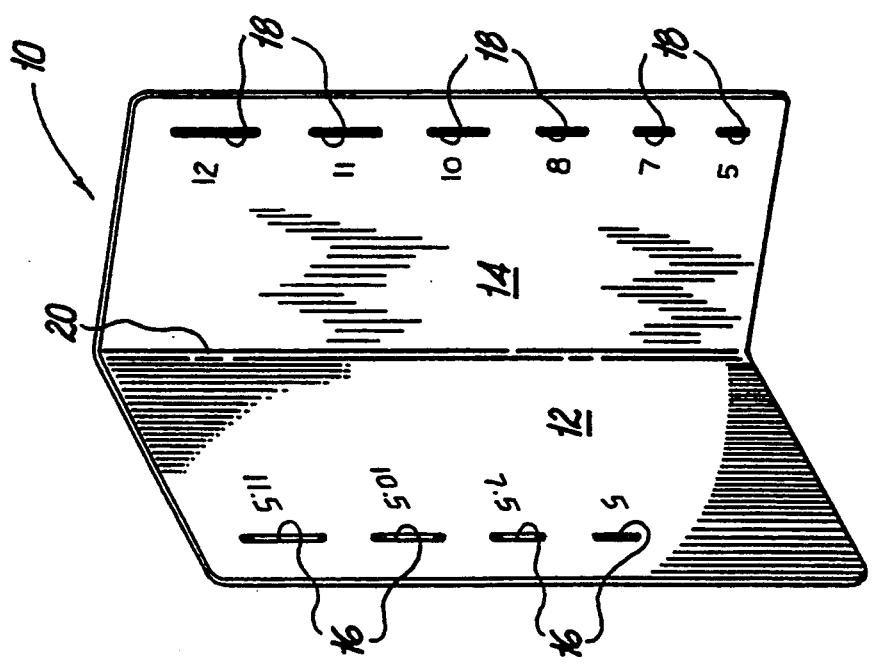
FIG. 1 is a perspective view of the present invention, illustrating the plate member and slotted openings.

Referring now to the drawings and, in particular, to FIGS. 1-3, there is illustrated a preferred embodiment of the present invention. Template 10 includes plate portions 12,14 having slotted openings 16,18 respectively. A bend line 20 separates portions 12,14. Template 10 may be made from polymeric materials and formed by known injection molding techniques, which techniques minimize the cost of manufacture and make it economically feasible to discard the template after use. It is also within the scope of the present invention to fabricate the template from a variety of other materials including, for example, surgical plastics, paper or stainless steel. Other fabrication techniques are also contemplated including, for example, stamping, vacuum forming, etc.

Slotted openings 16,18 are configured and adapted to receive a portion of the cutting edge of a scalpel or other incising instrument and guide the instrument during making of the incision. Slotted openings 16,18 retain at least a portion of the cutting edge therewithin to ensure the formation of the desired sized incision. Preferably, slotted openings 16,18 are disposed along the peripheral areas of their respective plate portions. The dimensions of slotted openings 16,18 vary, and thus, provide the capability of forming various sized incisions with the use of the single template. The dimensions of slotted openings 16,18 are identified in millimeters as shown in FIGS. 1-2, and begin at 5 millimeters and increase in increments to 12 millimeters.

Referring now to FIG. 3, the arrangement of plate portions 12,14 is illustrated. Plate portion 12 is preferably angularly displaced relative to plate portion 14. This is an advantageous feature in that during application of one of the plate portions against the patient's body, the other plate portion projects from the operative site and, as such, may be grasped by the user. Thus, the relative angular displacement of the plate portions provides a means to grasp and control template 10. In particular, the projecting plate portion may be held by the surgeon so that the template may be maneuvered around the body so as to align the desired slotted opening over the incision site and to secure the template firmly against the tissue surface when forming an incision. Further, this angular displacement coupled with the positioning of slotted openings 16,18 along the peripheral areas of their respective plate portions serve to remove the surgeon's hand from the path of the incising instrument during incising of the body tissue.

The angular displacement A of the plate portions may range in value from about 30° to about 150°. In a preferred embodiment, the angular displacement A is 120°. However, it is also possible for plate portions 12,14 to be in coincidence.

Template 10 has particular application in endoscopic procedures wherein an incision is to be made to access the abdominal cavity of the patient. In such a procedure, it is desirable to have the dimension of the incision approximate the operative dimension of the instrument(s) to be inserted within the incision. In endoscopic and laparoscopic surgery, it is desirable to establish a snug fit of bodily tissue around the cannula to minimize the release of fluids from the body. In addition, in laparoscopic surgery, in which insufflating gases are introduced into the abdominal cavity to raise the cavity wall away from vital organs, dimensioning of the incision will help to minimize escape of these gases from the body.

Further understanding of the significant features of template 10 of the present invention will become more readily apparent by the following description of the use of same in forming an incision in the abdominal cavity.

Initially, the dimension of the incision to be formed in the abdominal cavity is ascertained. For exemplary purposes, assume a 10 millimeter incision is to be made in the abdomen. Since the 10 millimeter slotted opening is disposed on plate portion 14, plate portion 14 is pressed against the abdomen. Due to the angular displacement of plate portion 12 relative to plate portion 14, plate portion 12 projects from the operative site. Plate portion 12 is grasped and the template is maneuvered around the operative site to align the desired 10 millimeter slotted opening over the targeted location. Preferably, projecting plate portion 12 is grasped along the outer edge to ensure that the surgeon's hand will not be in the way during incising of the patient. Thereafter, the cutting edge of an incising instrument is positioned within the desired 10 millimeter slotted opening. While holding the projecting plate portion 12 in a manner so that the template is pressed against the abdomen, the abdominal cavity is incised by applying a downward force and sliding motion to the scalpel. During the incising procedure, the slotted opening guides the cutting edge of the scalpel and retains the edge within the slotted opening to ensure that the incision will be of the desired dimension.

Figure 4:
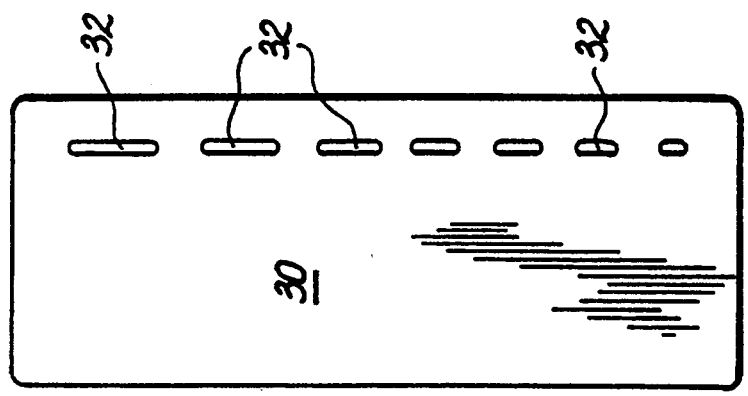
FIG. 4 is a top plan view of an alternative embodiment of the template of FIG. 1, illustrating "+"-shaped openings.
Figure 5:
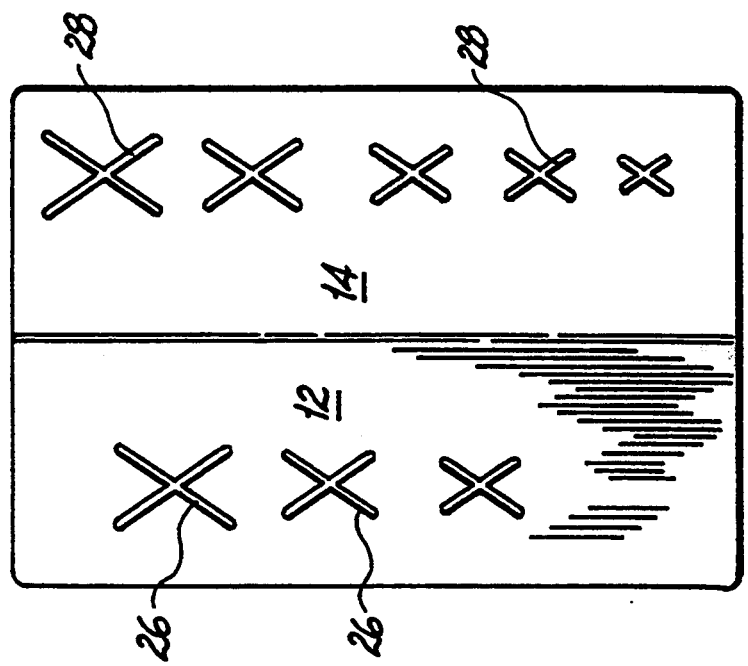
FIG. 5 is a top plan view of an alternative embodiment of the template of FIG. 1 illustrating "x"-shaped openings.

FIG. 4 illustrates an alternative embodiment of the template of FIG. 1, in which slotted openings 22,24 are configured in a "+"-shape to form an incision which generally corresponds to the circular dimension of the cannula. FIG. 5 illustrates another alternative embodiment having "x"-shaped slotted openings 26,28. Depending upon individual needs and preferences, any of the slotted openings may be used in each embodiment. In other respects, the embodiments shown in FIGS. 4 and 5 are essentially the same as the previously described embodiment.

Figure 6:
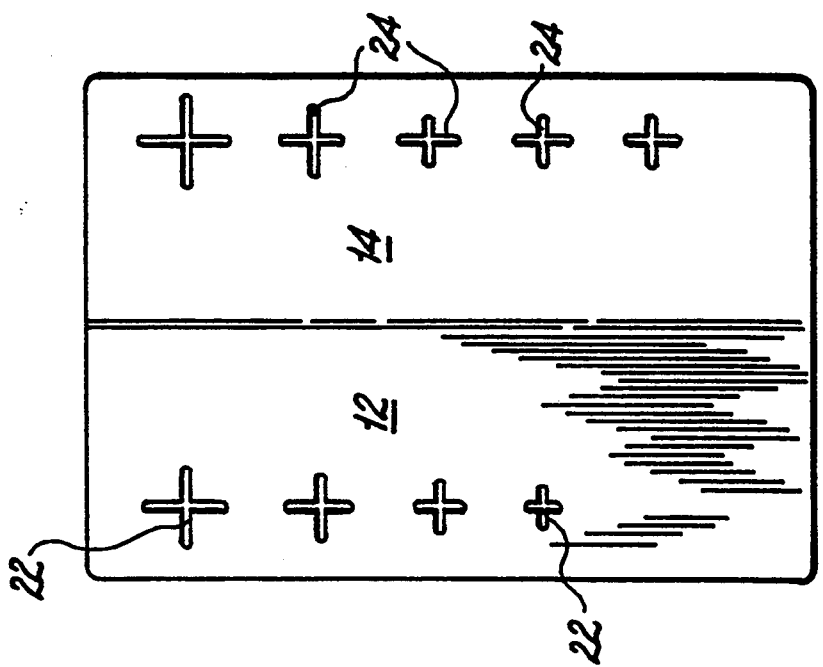
FIG. 6 is a top plan view of another alternative embodiment of the template of FIG. 1.

FIG. 6 illustrates an alternative embodiment of the template of FIG. 1, which includes only one plate portion 30 having slotted openings 32. Plate portion 30 may be held against the body cavity along the edges of the plate member and the incision formed in the same manner as described in the prior embodiment.

Figure 8:
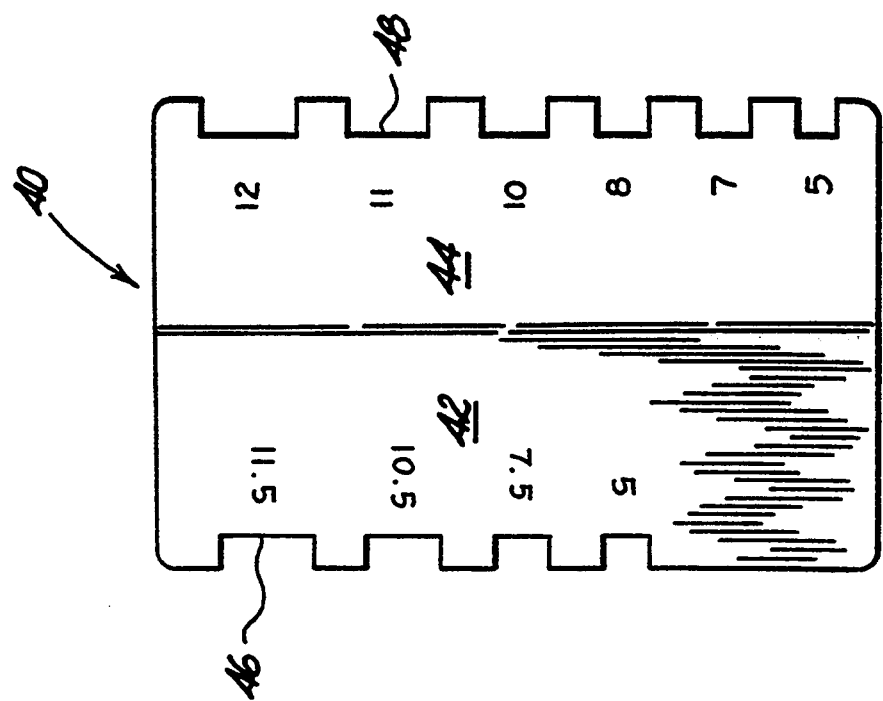
FIG. 8 is a top plan view of the embodiment of FIG. 7.
Figure 7:
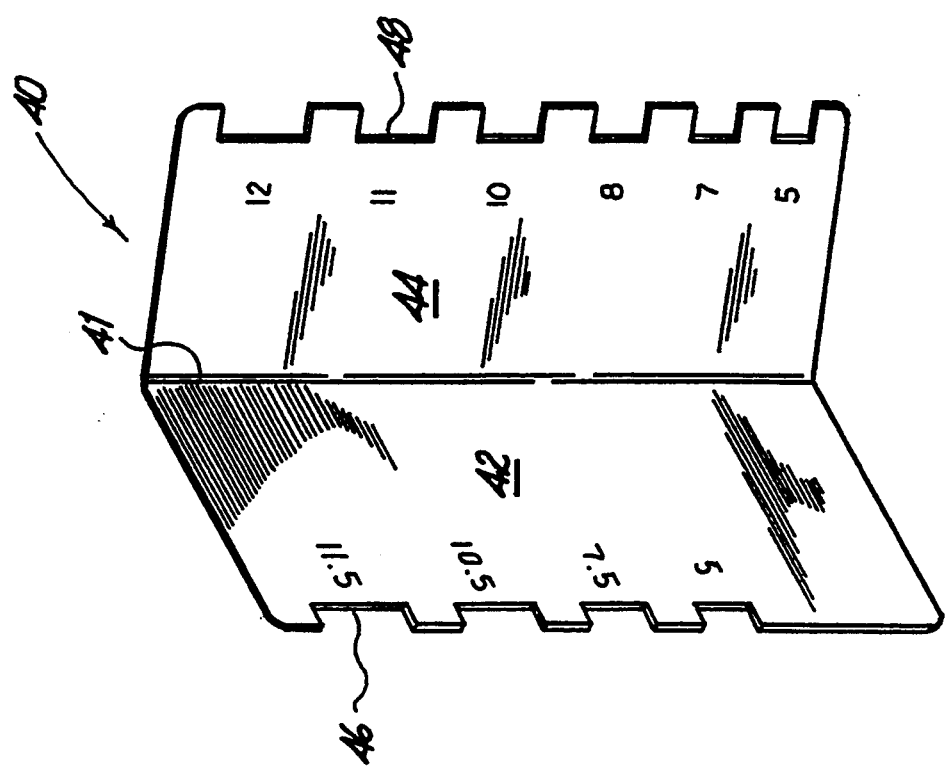
FIG. 7 is a perspective view of another embodiment of the present invention, illustrating recesses formed in the peripheral edges of the plate member.

FIGS. 7 and 8 illustrate another embodiment of the present invention. Template 40 has a bend line 41 separating plate portions 42 and 44. Plate portions 42,44 have recesses 46,48, respectively adapted to receive the cutting edge of an incising instrument. Recesses 46,48 are disposed along the peripheral edges of their respective plate portions. The particular dimensions of recesses 46, 48 are labelled in millimeters as shown. The angular displacement of plate portions 42 and 44 is in the range of the angular displacement A disclosed for the embodiment of FIGS. 1–3. However, it is also possible for plate portions 42,44 to be in coincidence.

Figure 10:
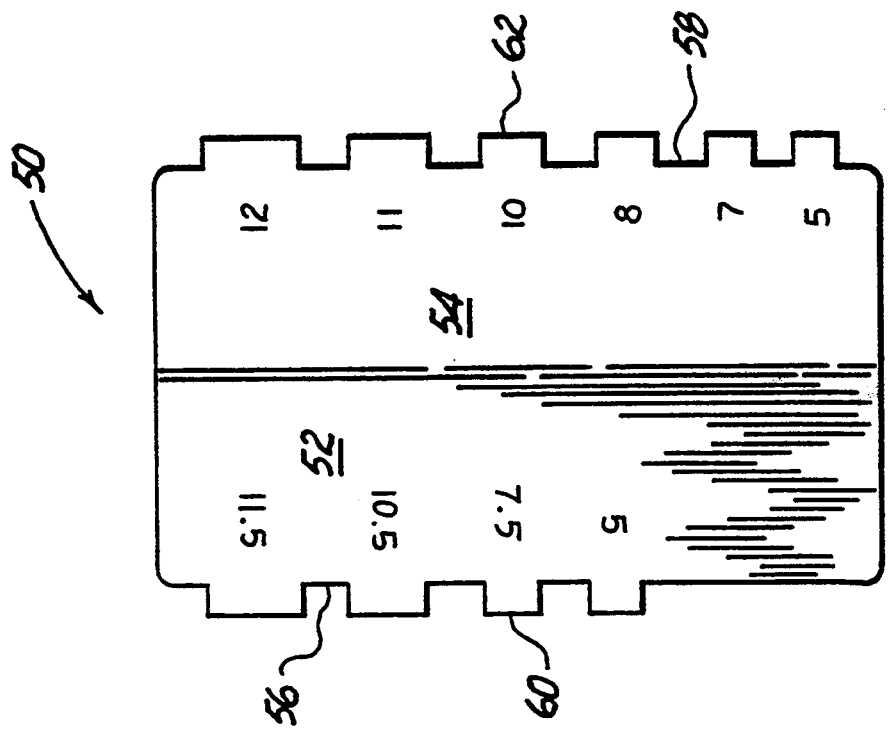
FIG. 10 is a top plan view of the embodiment of FIG. 9.
Figure 9:
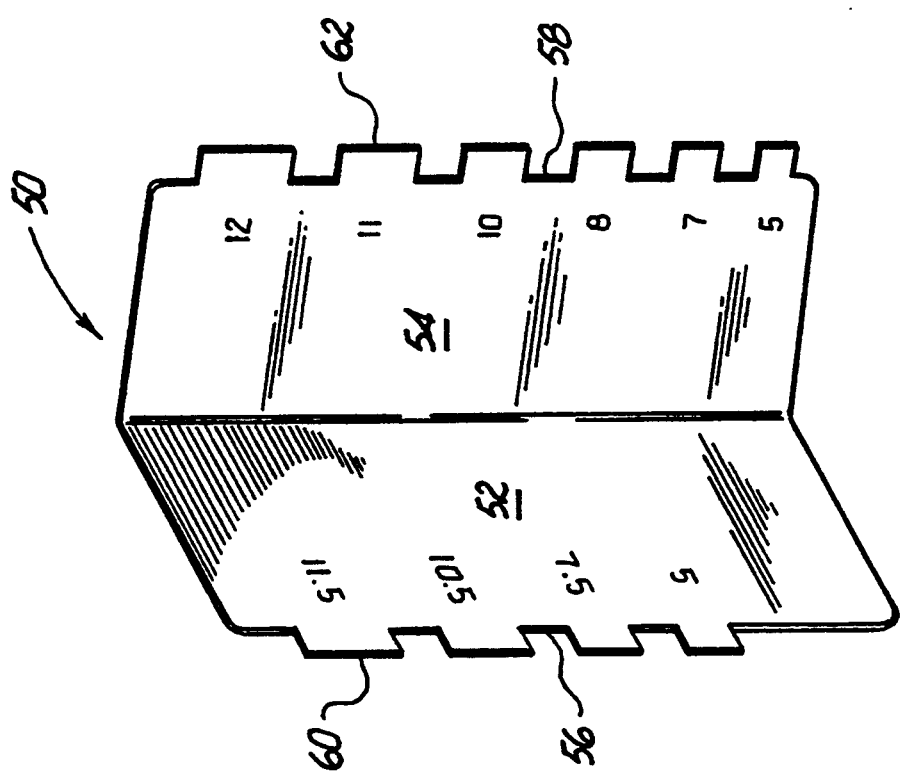
FIG. 9 is a perspective view of another embodiment of the present invention, illustrating co-planar projections extending from the peripheral edges of the plate member for measuring the size of an incision.

FIGS. 9 and 10 illustrate another alternative embodiment of the present invention. In accordance with this embodiment, plate portions 52, 54 of template 50 have recesses 56, 58, respectively, formed in their peripheral edges. Recesses 56,58 define extensions 60,62 respectively. Extensions 60, 62 may be used to measure the length of an incision and may be dimensioned to cover a range of incision lengths as shown in FIGS. 9 and 10. Thus, a surgeon may measure the length of an incision.

The invention in its broader aspects therefor is not limited to the specific embodiments herein shown and described but departures may be made therefrom within the scope of the accompanying claims without departing from the principles of the invention and without sacrificing its chief advantages.

What is claimed is:

1. A surgical template to assist in forming an incision of predetermined size in tissue, comprising a plate member defining a longitudinal axis and having a bend line which defines a first planar plate portion and a second planar plate portion, each said first and second plate portions having a longitudinal edge, at least one of said plate portions including at least two longitudinally extending slotted openings of predetermined lengths disposed adjacent said longitudinal edge thereof, each said at least two slotted openings dimensioned and configured to receive at least a portion of a cutting edge of an incising instrument to guide the instrument during an incising of the tissue.

2. The surgical template of claim 1, wherein the dimensions of said at least two slotted openings vary in increments to accommodate formation of various sized incisions.

3. The surgical template of claim 1, wherein the lengths of said at least two slotted openings range in value from about 5 millimeters to about 12 millimeters.

4. The surgical template of claim 1, wherein a plane defined by said first plate portion is angularly displaced relative to a plane defined by said second plate portion, whereby upon application of one plate portion against the tissue the other plate portion projects from said one plate portion and away from the tissue.

5. The surgical template of claim 4, wherein said plane defined by said first plate portion is displaced relative to said plane defined by said second plate portion by an angle ranging in value from about 30° to about 150°.

6. The surgical template of claim 5, wherein the angle defined by said planes of said first and second plate portions is about 120°.

7. The surgical template of claim 1 wherein said bend line is generally disposed in the center of said plate member.

8. A surgical template to assist in forming an incision of a predetermined size in tissue comprising a plate member having a longitudinal bend line generally disposed along a central longitudinal axis, said bend line defining a first planar plate portion and a second planar plate portion, said first and second plate portions each defining a plane and wherein said plane defined by said first plate portion is angularly displaced relative to said plane defined by said second plate portion such that upon application of one plate portion against the tissue the other plate portion projects from said one plate portion and away from the tissue in a position to be grasped by a user, each said first and second plate portions having a longitudinal peripheral edge, at least one of said first and second plate portions including at least two recesses formed in said peripheral edge thereof, each said at least two recesses defining an inner edge in general parallel relationship with said bend line and being configured and adapted for reception of at least a portion of a cutting edge of an incising instrument and for guiding the instrument during incising of the tissue.

9. The surgical template of claim 8, wherein the dimensions of said at least two recesses vary in increments to accommodate formation of various sized incisions.

10. The surgical template of claim 9, wherein the lengths of said at least two recesses range in value from about 5 millimeters to about 12 millimeters.

11. The surgical template of claim 8, wherein adjacent recesses define extensions therebetween, said extensions adapted for measuring the length of an incision formed in the tissue.

12. The surgical template of claim 11, wherein the dimension of said extensions vary in increments to accommodate measurement of various-sized incisions.

13. The surgical template of claim 12, wherein the dimensions of said extensions range in value from about 5 millimeters to about 12 millimeters.

14. A surgical temple to assist in forming an incision of a predetermined size in tissue, comprising a plate member having a bend line generally disposed along a central longitudinal axis thereof, said bend line defining a first planar plate portion and a second planar plate portion, said first and second plate portions each defining a plane and wherein said plane defined by said first plate portion is angularly displaced relative to said plane defined by said second plate portion such that upon application of one plate portion against the tissue the other plate portion projects from said one plate portion and away from the tissue in a position to be grasped by a user, each said first and second plate portions having a longitudinal peripheral edge, at least one of said first and second plate portions including a plurality of generally longitudinally extending slotted openings disposed adjacent said peripheral edge thereof, said slotted openings being configured and adapted for reception of at least a portion of a cutting edge of an incising instrument and for guiding the instrument during incising of the tissue.

15. A method for forming an incision of a predetermined size in tissue, the method comprising the steps of:
providing a surgical template including a plate member having a bend line generally disposed along a central longitudinal axis thereof, said bend line defining a first planar plate portion and a second planar plate portion, said first and second plate portions each defining a plane and wherein said plane defined by said first plate portion is angularly displaced relative to said plane defined by said second plate portion such that upon application of one plate portion against the tissue the other plate portion projects from said one plate portion and away from the tissue in a position to be grasped by a user, each said first and second plate portions having a longitudinal peripheral edge, at least one of said first and second plate portions including a plurality of generally longitudinally extending slotted openings disposed adjacent said peripheral edge thereof, said slotted openings being configured and dimensioned for reception of at least a portion of a cutting edge of an incising instrument and for guiding the instrument during incising of the tissue;

applying said one plate portion against the tissue such that said other plate portion projects therefrom in said position to be grasped by the user;

grasping said other plate portion projecting from the tissue and maneuvering said plate portions to align one of said slotted openings of said one plate portion over a targeted portion of the tissue;

applying the cutting edge of the incising instrument within said one slotted opening; and incising the tissue by applying a downward pressure to the incising instrument and sliding the instrument through said one slotted opening.

* * * * *